US007723579B2

(12) United States Patent
Chungu et al.

(10) Patent No.: US 7,723,579 B2
(45) Date of Patent: May 25, 2010

(54) CANOLA CULTIVAR DN040244

(75) Inventors: Chibwe Chungu, Visalia, CA (US);
Thomas J. Kubik, Saskatoon (CA)

(73) Assignee: Dow AgroSciences LLC, Indianapolis, IN (US)

( * ) Notice: Subject to any disclaimer, the term of this patent is extended or adjusted under 35 U.S.C. 154(b) by 110 days.

(21) Appl. No.: 12/102,716

(22) Filed: Apr. 14, 2008

(65) Prior Publication Data

US 2008/0263715 A1 Oct. 23, 2008

Related U.S. Application Data

(60) Provisional application No. 60/911,473, filed on Apr. 12, 2007.

(51) Int. Cl.
*A01H 5/00* (2006.01)
*C12N 15/82* (2006.01)

(52) U.S. Cl. ...................................... 800/306; 435/430

(58) Field of Classification Search ........................ None
See application file for complete search history.

(56) References Cited

U.S. PATENT DOCUMENTS

| | | | |
|---|---|---|---|
| 4,769,061 A | 9/1988 | Comai | |
| 4,810,648 A | 3/1989 | Stalker | |
| 4,940,835 A | 7/1990 | Shah | |
| 4,975,374 A | 12/1990 | Goodman | |
| 5,008,200 A | 4/1991 | Ranch | |
| 5,015,580 A | 5/1991 | Christou | |
| 5,024,944 A | 6/1991 | Collins | |
| 5,266,317 A | 11/1993 | Tomalski | |
| 5,322,783 A | 6/1994 | Tomes | |
| 5,339,294 A | 8/1994 | Rodgers | |
| 5,494,813 A | 2/1996 | Hepher | |
| 5,563,055 A | 10/1996 | Townsend | |
| 5,959,185 A | 9/1999 | Streit | |
| 5,973,234 A | 10/1999 | Mueller | |
| 5,977,445 A | 11/1999 | Soper | |
| 6,248,876 B1 | 6/2001 | Barry | |
| 6,455,763 B1 | 9/2002 | Sernyk | |
| 7,348,473 B2 | 3/2008 | Kubik | |
| 7,351,882 B2 * | 4/2008 | Patel | 800/306 |
| 7,355,100 B2 | 4/2008 | Kubik | |
| 7,456,339 B2 | 11/2008 | Patel | |
| 2006/0225146 A1 | 10/2006 | Kubik | |
| 2006/0225159 A1 | 10/2006 | Kubik | |

FOREIGN PATENT DOCUMENTS

| | | |
|---|---|---|
| EP | 0242246 B1 | 10/1987 |
| EP | 0333033 A1 | 9/1989 |
| WO | 9302197 A1 | 2/1993 |
| WO | 9319181 A1 | 9/1993 |
| WO | 9400992 A1 | 1/1994 |
| WO | 9516776 A1 | 6/1995 |
| WO | 9518855 A2 | 7/1995 |
| WO | 9630517 A1 | 10/1996 |
| WO | 9630530 A1 | 10/1996 |
| WO | 2005012515 A2 | 2/2005 |
| WO | 2005107437 A2 | 11/2005 |
| WO | 2007/016521 A2 | 2/2007 |

OTHER PUBLICATIONS

International Search Report, prepared for PCT/US2008/060124, dated Aug. 25, 2008.
Tavladoraki, Paraskevl, et al., "Transgenic plants expressing a functional single-chain Fv antibody are specifically protected from virus attack," Nature, vol. 366, pp. 469-472 (Dec. 2, 1993).
Teeri, T.H., et al., "Gene fusions to lacZ reveal new expression patterns of chimeric genes in transgenic plants," EMBO J., vol. 8, pp. 343-350 (1989).
Timko, M.P., et al., "Light regulation of plant gene expression by an upstream enhancer-like element," Nature, vol. 318, pp. 579 582 (Dec. 12, 1985).
Toubart, Patrick, et al., "Cloning and characterization of the gene encoding the endopolygalacturonase-inhibiting protein (PGIP) of Phaseolus vulgaris L.," Plant J., vol. 2, No. 3, pp. 367-373 (1992).
Twell, David, et al., "Isolation and expression of an anther-specific gene from tomato," Mol. Gen. Genetics, vol. 217, pp. 240 245 (1989).
Van Damme, Els J.M., et al., "Molecular cloning of mannose-binding lectins from Clivia miniata," Plant Molec. Biol., vol. 24, pp. 825-830 (1994).
Van Hartingsveldt, Wim, et al., "Cloning, characterization and overexpression of the phytase-encoding gene (phyA) of Aspergillus niger," Gene, vol. 127, pp. 87-94 (1993).
Van Den Elzen, Peter J.M., et al., "A chimaeric hygromycin resistance gene as a selectable marker in plant cells," Plant Mol. Biol., vol. 5, pp. 299-302 (1985).
Velten, J., et al., "Isolation of a dual plant promoter fragment from the Ti plasmid of Agrobacterium tumefaciens," EMBO J., vol. 3, No. 12, pp. 2723 2730 (1984).
Ward, E.R., et al., "Chemical regulation of transgene expression in plants," Plant Mol. Biol., vol. 22, pp. 361 366 (1993).
Zhang, Li-Jian, et al., "Efficient Transformation of Tobacco by Ultrasonication," Bio/Technology, vol. 9, pp. 996-997 (1991).
Klein, Theodore M., et al., "Transformation of Microbes, Plants and Animals by Particle Bombardment," Biotechnology, vol. 10, pp. 286-291 (Mar. 1992).
Knox, Cheryl A.P., et al., "Structure and Organization of Two Divergent α Amylase Genes from Barley," Plant Mol. Biol., vol. 9, pp. 3 17 (1987).
Knutzon, Deborah S., et al., "Modification of Brassica seed oil by antisense expression of a stearoyl-acyl carrier protein desaturase gene," Proc. Natl. Acad. Sci. U.S.A., vol. 89, pp. 2624-2628 (Apr. 1992).
Komatsuda, Takao, et al., "Genotype X Sucrose Interactions for Somatic Embryogenesis in Soybeans," Crop Sci., vol. 31, pp. 333 337 (1991).

(Continued)

*Primary Examiner*—Elizabeth F McElwain
(74) *Attorney, Agent, or Firm*—Kenneth B. Ludwig; TraskBritt

(57) ABSTRACT

The present invention relates to a new and distinctive canola cultivar, designated DN040244. Also included are seeds of canola cultivar DN040244, to the plants, or plant parts, of canola DN040244 and to methods for producing a canola plant produced by crossing the canola DN040244 with itself or another canola cultivar, and the creation of variants by mutagenesis or transformation of canola DN040244.

20 Claims, No Drawings

OTHER PUBLICATIONS

Komatsuda, Takao, et al., "Maturation and Germination of Somatic Embryos as Affected by Sucrose and Plant Growth Regulators in Soybeans Glycine gracilis Skvortz and Glycine max (L.) Merr." Plant Cell, Tissue and Organ Culture, vol. 28, pp. 103 113 (1992).

Koncz, Csaba, et al., "Expression and assembly of functional bacterial luciferase in plants," Proc. Natl. Acad. Sci U.S.A., vol. 84, pp. 131-135 (Jan. 1987).

Kramer, Karl J., et al., "Sequence of a cDNA and Expression of the Gene Encoding Epidermal and Gut Chitinases of Manduca sexta," Insect Biochem. Molec. Biol., vol. 23, pp. 691-701 (1993).

Lamb, Christopher J., et al., "Emerging Strategies for Enhancing Crop Resistance to Microbial Pathogens," Bio/Technology, vol. 10, pp. 1436-1445 (Nov. 1992).

Last, D.I., et al., "pEmu: an improved promoter for gene expression in cereal cells," Theor. Appl. Genet., vol. 81, pp. 581 588 (1991).

Lee, Kathleen Y., et al., "The molecular basis of sulfonylurea herbicide resistance," EMBO J., vol. 7, pp. 1241-1248 (1988).

Lepetit, Marc, et al., "A plant histone gene promoter can direct both replication-dependent and -independent gene expression in transgenic plants," Mol: Gen. Genetics, vol. 231, pp. 276 285 (1992).

Lerner, David R., et al., "Cloning and Characterization of Root-Specific Barley Lectin," Plant Physiol., vol. 91, pp. 124 129 (1989).

Logemann, J., et al., "Expression of a Barley Ribosome-Inactivating Protein Leads to Increased Fungal Protection in Transgenic Tobacco Plants," Bio/Technology, vol. 10, pp. 305-308 (1992).

Marshall, L.C., et al., "Allelic mutations in acetyl-coenzyme A carboxylase confer herbicide tolerance in maize," Theor. Appl. Genet., vol. 83, pp. 435-442 (1992).

Martin, Gregory B., et al., "Map-Based Cloning of a Protein Kinase Gene Conferring Disease Resistance in Tomato," Science, vol. 262, pp. 1432-1436 (Nov. 26, 1993).

Matsuoka, Ken, et al., "Propeptide of a precursor to a plant vacuolar protein required for vacuolar targeting," Proc. Natl. Acad. Sci., vol. 88, pp. 834-838 (Feb. 1991).

McElroy, David, et al., "Isolation of an Efficient Actin Promoter for Use in Rice Transformation," Plant Cell, vol. 2, pp. 163 171 (Feb. 1990).

Mett, Vadim L., et al., "Copper-controllable gene expression system for whole plants," PNAS, vol. 90, pp. 4567 4571 (May 1993).

Miki, B.L., et al., "Procedures for Introducing Foreign DNA into Plants" in Methods in Plant Molecular Biology and Biotechnology, Glick B. R. and Thompson, J. E., Eds., CRC Press, Inc., Boca Raton, pp. 67-88 (1993).

Miki, B.L., et al., "Transformation of *Brassica napus* canola cultivars with *Arabidopsis thaliana* acetohydroxyacid synthase genes and analysis of herbicide resistance," Theor. Appl. Genet., vol. 80, pp. 449-458 (1990).

Mindrinos, Michael, et al., "The *A. thaliana* Disease Resistance Gene RPS2 Encodes a Protein Containing a Nucleotide-Binding Site and Leucine-Rich Repeats," Cell, vol. 78, pp. 1089-1099 (Sep. 23, 1994).

Moloney, Marice M., et al., "High efficiency transformation of *Brassica napus* using Agrobacterium vectors," Plant Cell Reports, vol. 8, pp. 238-242 (1989).

Murai, Norimoto, et al., "Phaseolin Gene from Bean Is Expressed After Transfer to Sunflower Via Tumor-Inducing Plasmid Vectors," Science, vol. 222, pp. 476 482 (Nov. 4, 1983).

Naleway, J.J., et al., "Detection of GUS Gene Expression In Transformed Plant Cells With New Lipophilic, Fluorogenic β-Glucuronidase Substrate," J. Cell Biol., vol. 115, p. 151a (1991).

Narasimhulu, S.B., et al., "Species Specific Shoot Regeneration Response of Cotyledonary Explants of Brassicas", Plant Cell Reports, vol. 7, pp. 107-106 (Spring 1988).

Odell, Joan T., et al., "Identification of DNA sequences required for activity of the cauliflower mosaic virus 35S promoter," Nature, vol. 313, pp. 810 812 (Feb. 28, 1985).

Pandey, Punita, et al., "Plant Regeneration from Leaf and Hypocotyl Explants of *Glycine wightii* (W. and A.) VERDC. var. longicauda," Japan J. Breed., vol. 42, pp. 1 5 (1992).

Pang, Sheng-Zhi, et al., "Expression of a gene encoding a scorpion insectotoxin peptide in yeast, bacteria and plants," Gene, vol. 116, pp. 165-172 (1992).

Pen, Jan, et al., "Production of Active Bacillus Licheniformis Alpha-Amylase in Tobacco and its Application in Starch Liquefaction," Bio/Technology, vol. 10, pp. 292-296 (Mar. 1992).

Pratt, Grahame E., et al., "Identification of an Allatostatin from Adult Diploptera Punctata," Biochem. Biophys. Res. Comm., vol. 163, pp. 1243-1247 (Sep. 29, 1989).

Przibilla, Elisabeth, et al., "Site-Specific Mutagenesis of the D1 Subunit of Photosystem II in Wild-Type Chlamydomonas," Plant Cell, vol. 3, pp. 169-174 (Feb. 1991).

Raboy, V., et al., "A Survey of Maize Kernel Mutants for Variation in Phytic Acid," Maydica, vol. 35, pp. 383-390 (1990).

Reagan, Jeff D., "Expression Cloning of an Insect Diuretic Hormone Receptor," J. Biol. Chem., vol. 269, No. 1, pp. 9-12 (1994).

Sanford, J.C., "Biolistic plant transformation," Physiol Plant, vol. 79, pp. 206-209 (1990).

Sanford, John C., "The biolistic process," Trends Biotech., vol. 6, pp. 299-302 (Dec. 1988).

Schena, Mark, et al., "A steroid-inducible gene expression system for plant cells," Proc. Natl. Acad. Sci. U.S.A., vol. 88, pp. 10421-10425 (Dec. 1991).

Sengupta-Gopalan, Champa, et al., "Developmentally regulated expression of the bean β-phaseolin gene in tobacco seed," Proc. Natl. Acad. Sci. U.S.A., vol. 82, pp. 3320 3324 (May 1985).

Shah, Dilip M., et al., "Engineering Herbicide Tolerance in Transgenic Plants," Science, vol. 233, pp. 478-481 (Jul. 25, 1986).

Shetty, K., et al., "Stimulation of In Vitro Shoot Organogenesis in Glycine max (Merrill.) by Allantoin and Amides," Plant Science, vol. 81, pp. 245 251 (1992).

Shiroza, Teruaki, et al., "Sequence Analysis of the Streptococcus mutans Fructosyltransferase Gene and Flanking Regions," J. Bacteol., vol. 170, No. 2, pp. 810-816 (Feb. 1988).

Simpson, June, et al., "Light-inducible and tissue-specific expression of a chirnaeric gene under control of the 5'-flanking sequence of a pea chlorophyll a/b-binding protein gene," EMBO J., vol. 4, No. 11, pp. 2723 2729 (1985).

Søgaard, Morten, et al., "Site-directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-Amylase 1," J. Biol. Chem., vol. 268, No. 30, pp. 22480-22484 (1993).

Spencer, T. Michael, et al., "Production of fertile transgenic maize by electroporation of suspension culture cells," Plant Mol. Biol., vol. 24, pp. 51 61 (1994).

Stalker, David M., et al., "Herbicide Resistance in Transgenic Plants Expressing a Bacterial Detoxification Gene," Science, vol. 242, pp. 419 423 (Oct. 21, 1988).

Stiefel, Virginia, et al., "Expression of a maize cell wall hydroxyproline rich glycoprotein gene in early leaf and root vascular differentiation," Plant Cell, vol. 2, pp. 785 793 (Aug. 1990).

Steinmetz, Michel, et al., "The DNA sequence of the gene for the secreted *Bacillus subtilis* enzyme levansucrase and its genetic control sites," Mol. Gen. Genet., vol. 20, pp. 220-228 (1985).

Stephens, P.A., et al., "Agronomic Evaluation of Tissue Culture Derived Soybean Plants," Theor. Appl. Genet., vol. 82, pp. 633 635 (1991).

Sumitani, Jun-ichi, et al., "Molecular Cloning and Expression of Proteinaceous α-Amylase Inhibitor Gene from Streptomyces nitrosporeus in *Escherichia coli*," Biosci. Biotech. Biochem., vol. 57, pp. 1243-1248 (1993).

Svab, Zora, et al., "Aminoglycoside-3"-adenyltransferace confers resistance to spectinomycin and streptomycin in *Nicotiana tabacum*, Plant Mol. Biol., vol. 14, pp. 197-205 (1990).

Swanson, Eric B., "Microspore Culture in Brassica," in Methods in Molecular Biology, vol. 6, Chapter 17, pp. 159-169 (1990).

Abe, Keiko, et al., "Molecular Cloning of a Cysteine Proteinase Inhibitor of Rice (Oryzacystatin)," J. Biol. Chem., vol. 262, No. 35, pp. 16793-16797 (Dec. 15, 1987).

Atanassova, Rossitza, et al., "A 126 bp fragment of a plant histone gene promoter confers preferential expression in meristems of transgenic Arabidopsis," The Plant Journal, vol. 2, No. 3, pp. 291 300 (1992).

Barsby, T.L., et al., "A Rapid and Efficient Alternative Procedure for the Regeneration of Plants from Hypocotyl Protoplasts of Brassica napus", Plant Cell Reports, vol. 5, pp. 101-103, 1986.

Beachy, Roger N., et al., "Coat Protein-Mediated Resistance Against Virus Infection," Ann. Rev. Phytopathol., vol. 28, pp. 451-474 (1990).

Becker, Thomas W., et al., "The cab-m7 gene: a light-inducible, mesophyll-specific gene of maize," Plant Mol. Biol. 20:49 (1992).

Botella, Jose R., et al., "Differential expression of two calmodulin genes in response to physical and chemical stimuli," Plant Molec. Biol., vol. 24, pp. 757-766 (1994).

Chalfie, Martin, et al., "Green Fluorescent Protein as a Marker for Gene Expression," Science, vol. 263, pp. 802-805 (Feb. 11, 1994).

Charest, Pierre J., et al., "In vitro study of transgenic tobacco expressing Arabidopsis wild type and mutant acetohydroxyacid synthase genes," Plant Cell Rep., vol. 8, pp. 643-646 (1990).

Christensen, Alan H., et al., "Sequence analysis and transcriptional regulation by heat shock of polyubiquitin transcripts from maize," Plant Mol. Biol., vol. 12, pp. 619 632 (1989).

Christensen, Alan H., et al., "Maize polyubiquitin genes: structure, thermal perturbation of expression and transcript splicing, and promoter activity following transfer to protoplasts by electroporation," Plant Mol. Biol., vol. 18, pp. 675 689 (1992).

Christou, Paul, et al., "Stable transformation of soybean by electroporation and root formation from transformed callus," Proc. Natl. Acad. Sci. U.S.A., vol. 84, pp. 3962-3966 (Jun. 1987).

Comai, L., et al., "Expression in plants of a mutant aroA gene from Salmonella typhimurium confers tolerance to glyphosate," Nature, vol. 317, pp. 741 744 (Oct. 24, 1985).

Creissen, Gary, et al., "Molecular characterization of glutathione reductase cDNAs from pea (Pisum sativum L.)," Plant J., vol. 2, No. 1, pp. 129-131 (1991).

D'Halluin, Kathleen, et al., "Transgenic Maize Plants by Tissue Electroporation," Plant Cell, vol. 4, pp. 1495 1505 (Dec. 1992).

DeBlock, Marc, et al., "Expression of foreign genes in regenerated plants and in their progeny," EMBO J., vol. 3, No. 8, pp. 1681-1689 (1984).

DeGreef, Willy, et al., "Evaluation of Herbicide Resistance in Transgenic Crops Under Field Conditions," Bio/Technology, vol. 7, pp. 61-64 (Jan. 1989).

DeShayes, Alain, et al., "Liposome-mediated transformation of tobacco mesophyll protoplasts by an *Escherichia coli* plasmid," EMBO. J., vol. 4, pp. 2731-2737 (1985).

DHIR, Sarwan K., et al., "Regeneration of Fertile Plants from Protoplasts of Soybean (Glycine max L. Merr.): Genotypic Differences in Culture Response," Plant Cell Reports, vol. 11, pp. 285-289, (1992).

Draper, J., et al., "Ti Plasmid Homologous Sequences Present in Tissues from Agrobacterium Plasmid-transformed Petunia Protoplasts," Plant & Cell Physiol., vol. 23, pp. 451-458 (1982).

Eichholtz, David A., et al., "Expression of Mouse Dihydrofolate Reductase Gene Confers Methotrexate Resistance in Transgenic Petunia Plants," Somatic Cell Mol. Genet., vol. 13, No. 1, pp. 67-76 (1987).

Elliot, Kathryn J., et al., "Isolation and characterization of fruit vacuolar invertase genes from two tomato species and temporal differences in mRNA levels during fruit ripening," Plant Molec. Biol., vol. 21, pp. 515-524 (1993).

Fisher, Dane K., et al., "Starch Branching Enzyme II from Maize Endosperm," Plant Physiol., vol. 102, pp. 1045-1046 (1993).

Fontes, Elizabeth B.P., et al., "Characterizaton of an Immunoglobulin Binding Protein Homolog in the Maize floury-2 Endosperm Mutant," Plant Cell, vol. 3, pp. 483 496 (May 1991).

Fraley, Robert T., et al., "Expression of bacterial genes in plant cells," Proc. Natl. Acad. Sci. U.S.A., vol. 80, pp. 4803-4807 (Aug. 1983).

Gatz, Christiane, et al., "Regulation of a modified CaMV 35S promoter by the Tn10-encoded Tet repressor in transgenic tobacco," Mol. Gen. Genetics, vol. 227, pp. 229 237 (1991).

Gatz, Christiane, et al., Efficiency of the tetracycline-dependent gene expression system: complete suppression and efficient induction of the rolB phenotype in transgenic plants, Mol. Gen. Genetics, vol. 243, pp. 32 38 (1994).

Geiser, Martin, et al., "The hypervariable region in the genes coding for entomopathogenic crystal proteins of *Bacillus thuringiensis*; nucleotide sequence of the kurhd1 gene of subsp. kurstaki HD1," Gene, vol. 48, pp. 109-118 (1986).

Glick and Thompson, Methods in Plant Molecular Biology and Biotechnology, CRC Press, Boca Raton, pp. 269-285 (1993).

Gordon-Kamm, William J., et al., "Transformation of Maize Cells and Regeneration of Fertile Transgenic Plants," Plant Cell, vol. 2, pp. 603 618 (Jul. 1990).

Gould, Stephen J., et al., "A Conserved Tripeptide Sorts Proteins to Peroxisomes," J. Cell. Biol., vol. 108, pp. 1657-1664 (May 1989).

Griess, Eike A., et al., "Isolation and Sequence Comparison of a Maize Calmodulin cDNA," Plant Physiol., vol. 104, pp. 1467-1468 (1994).

Gruber, Margaret Y., et al., "Vectors for Plant Transformation" in Methods in Plant Molecular Biology and Biotechnology, Glick B. R. and Thompson, J. E., Eds., CRC Press, Inc., Boca Raton, pp. 89-119 (1993).

Guerrero, Felix D., et al., "Promoter sequences from a maize pollen-specific gene direct tissue-specific transcription in tobacco," Mol. Gen. Genetics, vol. 244, pp. 161 168 (1993).

Hain, R., et al., "Uptake, integration, expression and genetic transmission of a selectable chimaeric gene by plant protoplasts," Mol. Gen. Genet., vol. 199, pp. 161-168 (1985).

Hammock, Bruce D., et al., "Expression and effects of the juvenile hormone esterase in a baculovirus vector," Nature, vol. 344, pp. 458-461 (Mar. 29, 1990).

Hayes, John D., et al., "Molecular cloning and heterologous expression of a cDNA encoding a mouse glutathione S-transferase Yc subunit possessing high catalytic activity for aflatoxin B1-8,9-epoxide," Biochem. J., vol. 285, pp. 173-180 (1992).

Hayford, Maria B., et al., "Development of a Plant Transformation Selection System Based on Expression of Genes Encoding Gentamicin Acetyltransferases," Plant Physiol., vol. 86, pp. 1216-1222 (1988).

Heney, Gayle, et al., "The Purification of Avidin and its Derivatives on 2-Iminobiotin-6-aminohexyl-Sepharose 4B," Anal. Biochem., vol. 114, pp. 92 6 (1981).

Hille, Jacques, et al., "Bleomycin resistance: a new dominant selectable marker for plant cell transformation," Plant Mol. Biol., vol. 7, pp. 171-176 (1986).

Horsch, R.B., et al., "A Simple and General Method for Transferring Genes into Plants," Science, vol. 227, pp. 1229-1231 (Mar. 8, 1985).

Huub J.M. Linthorst, et al., "Tobacco proteinase inhibitor I genes are locally, but not systemically induced by stress," Plant Molec. Biol., vol. 21, pp. 985-992 (1993).

Jaynes, Jesse M., et al., "Expression of a Cecropin B lytic peptide analog in transgenic tobacco confers enhanced resistance to bacterial wilt caused by Pseudomonas solanacearum," Plant Sci., vol. 89, pp. 43-53 (1993).

Jefferson, Richard A., "Assaying Chimeric Genes in Plants: The GUS Gene Fusion System," Plant Mol. Biol. Rep., vol. 5, No. 4, pp. 387-405 (1987).

Jones, Jonathan D.G., et al., "A dominant nuclear streptomycin resistance marker for plant cell transformation," Mol. Gen. Genet., vol. 210, pp. 86-91 (1987).

Jones, David A., et al., "Isolation of the Tomato Cf-9 Gene for Resistance to Cladosporium fulvum by Transposon Tagging," Science, vol. 266, pp. 789-793 (Nov. 4, 1994).

Kado, Carence I., "Molecular Mechanisms of Crown Gall Tumorigenesis," Crit. Rev. Plant Sci., vol. 10, No. 1, pp. 1-32 (1991).

Kalderon, Daniel, et al., "A short amino acid sequence able to specify nuclear location," Cell, vol. 39, pp. 499 509 (Dec. 1984).

Kartha, K.K., et al., "In vitro Plant Formation from Stem Explants of Rape (Brassica napus cv. Zephyr)," Physiol. Plant, vol. 31, pp. 217 220 (1974).

Kawalleck, Petra, et al., "Polyubiquitin gene expression and structural properties of the ubi4-2 gene in Petroselinum crispum," Plant Molec. Biol., vol. 21, pp. 673-684 (1993).

Klein, T.M., et al., "Factors Influencing Gene Delivery into Zea Mays Cells by High-Velocity Microprojectiles," Bio/Technology, vol. 6, pp. 559 563 (May 1988).

\* cited by examiner

CANOLA CULTIVAR DN040244

CROSS-REFERENCE TO RELATED APPLICATION

This application claims the benefit under 35 U.S.C. §119(c) of U.S. Provisional Application No. 60/911,473, filed Apr. 12, 2007, which is incorporated herein by reference.

FIELD OF THE INVENTION

The present invention relates to a new and distinctive canola cultivar, designated DN040244.

BACKGROUND OF THE INVENTION

Canola is a genetic variation of rapeseed developed by Canadian plant breeders specifically for its nutritional qualities, particularly its low level of saturated fat. In 1956 the nutritional aspects of rapeseed oil were questioned, especially concerning the high eicosenoic and erucic fatty acid contents.

In the early 1960's, Canadian plant breeders isolated rapeseed plants with low eicosenoic and erucic acid contents. The Health and Welfare Department recommended conversion to the production of low erucic acid varieties of rapeseed. Industry responded with a voluntary agreement to limit erucic acid content to five percent in food products, effective Dec. 1, 1973.

In 1985, the U.S. Food and Drug Administration recognized rapeseed and canola as two different species based on their content and uses. Rapeseed oil is used in industry, while canola oil is used for human consumption. High erucic acid rapeseed (HEAR) oil contains 22-60 percent erucic acid, while low erucic acid rapeseed (LEAR) oil has less than 2 percent erucic acid. Meal with less than 30 µmol/g glucosinolates is from canola. Livestock can safely eat canola meal, but high glucosinolate rapeseed meal should only be fed to cattle because it may cause thyroid problems in monogastric livestock.

Each canola plant produces yellow flowers that, in turn, produce pods, similar in shape to pea pods about ⅕th the size. Within the pods are tiny round seeds that are crushed to obtain canola oil. Each seed contains approximately 40 percent oil. The remainder of the seed is processed into canola meal, which is used as a high protein livestock feed.

Because it is perceived as a "healthy" oil, its use is rising steadily both as a cooking oil and in processed foods. The consumption of canola oil is expected to surpass corn and cottonseed oils, becoming second only to soybean oil. It is low in saturates, high in monounsaturates, and contains a high level of oleic acid. Many people prefer the light color and mild taste of canola oil over olive oil, the other readily available oil high in monounsaturates.

Rapeseed has been grown in India for more than 3000 years and in Europe since the 13th century. The 1950s saw the start of large scale rapeseed production in Europe. Total world rapeseed/canola production is more than 22.5 million metric tons.

Farmers in Canada began producing canola oil in 1968. Early canola cultivars were known as single zero cultivars because their oil contained 5 percent or less erucic acid, but glucosinolates were high. In 1974, the first licensed double zero cultivars (low erucic acid and low glucosinolates) were grown. Today all canola cultivars are double zero cultivars. Canola has come to mean all rapeseed cultivars that produce oil with less than 2 percent erucic acid and meal with less than 30 µmol/g of glucosinolates.

Canola production uses small grain equipment, limiting the need for large investments in machinery. Planting costs of canola are similar to those for winter wheat. The low investment costs and increasing consumer demand for canola oil make it a potentially good alternative crop.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior canola cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same canola traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new canola cultivars.

The development of new canola cultivars requires the development and selection of canola varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Canola, *Brassica napus oleifera annua*, is an important and valuable field crop. Thus, a continuing goal of plant breeders is to develop stable, high yielding canola cultivars that are agronomically sound. The reasons for this goal are obviously to maximize the amount of grain produced on the land used and to supply food for both animals and humans. To accomplish this goal, the canola breeder must select and develop canola plants that have the traits that result in superior cultivars.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided a novel canola cultivar designated DN040244. This invention thus relates to the seeds of canola cultivar DN040244, to the plants, or plant parts, of canola DN040244 and to methods for producing a canola plant produced by crossing the canola DN040244 with itself or another canola cultivar, and the creation of variants by mutagenesis or transformation of canola DN040244.

Thus, any such methods using the canola variety DN040244 are part of this invention: selfing, backcrosses, hybrid production, crosses to populations, and the like. All plants produced using canola variety DN040244, as a parent, are within the scope of this invention. Advantageously, the canola variety could be used in crosses with other, different, canola plants to produce first generation ($F_1$) canola hybrid seeds and plants with superior characteristics.

In another aspect, the present invention provides for single or multiple gene converted plants of DN040244. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, and industrial usage. The gene may be a naturally occurring canola gene or a transgene introduced through genetic engineering techniques.

In another aspect, the present invention provides regenerable cells for use in tissue culture of canola plant DN040244. The tissue culture will preferably be capable of regenerating plants having the physiological and morphological characteristics of the foregoing canola plant, and of regenerating plants having substantially the same genotype as the foregoing canola plant. Preferably, the regenerable cells in such tissue cultures will be embryos, protoplasts, meristematic cells, callus, pollen, leaves, anthers, roots, root tips, flowers, seeds, pods or stems. Still further, the present invention provides canola plants regenerated from the tissue cultures of the invention.

In another aspect, the present invention provides a method of introducing a desired trait into canola cultivar DN040244 wherein the method comprises: crossing a DN040244 plant with a plant of another canola cultivar that comprises a desired trait to produce $F_1$ progeny plants, wherein the desired trait is selected from the group consisting of male sterility, herbicide resistance, insect resistance, and resistance to bacterial disease, fungal disease or viral disease; selecting one or more progeny plants that have the desired trait to produce selected progeny plants; crossing the selected progeny plants with the DN040244 plants to produce backcross progeny plants; selecting for backcross progeny plants that have the desired trait and physiological and morphological characteristics of canola cultivar DN040244 to produce selected backcross progeny plants; and repeating these steps to produce selected first or higher backcross progeny plants that comprise the desired trait and all of the physiological and morphological characteristics of canola cultivar DN040244 as shown in Tables 1, 2, and 3. Included in this aspect of the invention is the plant produced by the method wherein the plant has the desired trait and all of the physiological and morphological characteristics of canola cultivar DN040244 as shown in Tables 1, 2, and 3.

In another aspect, the present invention comprises a canola cultivar comprising imidazolinone resistance and oleic acid content of greater than 70%. Preferably the canola cultivar further comprises protein value of greater than 45%, high yield (i.e., similar or superior to WCC/RRc check (46A65 and Q2), glucosinolate value of less than 12%, chlorophyll value of less than 18%, less than 3% linolenic acid and oleic acid content of greater than 70%. More preferably, the canola cultivar further comprises blackleg (*Leptosphaeria maculans*) resistance, Fusarium wilt and White Rust tolerance, and Clearfield herbicide trait. In a particular embodiment, the yield is greater than about 2100 kg/ha.

In another aspect, the present invention comprises a canola hybrid comprising imidazoline resistance and oleic acid content of greater than 70%. Preferably the canola hybrid further comprises protein value of greater than 45%, high yield (i.e., similar or superior to WCC/RRc check (46A65 and Q2), glucosinolate value of less than 12%, chlorophyll value of less than 18%, less than 3% linolenic acid and oleic acid content of greater than 70%. More preferably, the canola cultivar further comprises blackleg (*Leptosphaeria maculans*) resistance, Fusarium wilt and White Rust tolerance, and Clearfield herbicide trait. In a particular embodiment, the yield is greater than about 2100 kg/ha.

In addition to the exemplary aspects and embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Anther arrangement. The orientation of the anthers in fully opened flowers can also be useful as an identifying trait. This can range from introse (facing inward toward pistil), erect (neither inward not outward), or extrose (facing outward away from pistil).

Anther dotting. The presence/absence of anther dotting (colored spots on the tips of anthers) and if present, the percentage of anther dotting on the tips of anthers in newly opened flowers is also a distinguishing trait for varieties.

Anther fertility. This is a measure of the amount of pollen produced on the anthers of a flower. It can range from sterile (such as in female parents used for hybrid seed production) to fertile (all anthers shedding).

AOM hours. A measure of the oxidative stability of an oil using currently accepted Official Methods of the American Oil Chemists' Society (e.g., AOCS 12b-92).

Backcrossing. Backcrossing is a process in which a breeder repeatedly crosses hybrid progeny back to one of the parents, for example, a first generation hybrid $F_1$ with one of the parental genotypes of the $F_1$ hybrid.

Blackleg. Resistance to blackleg (*Leptosphaeria maculans*) is measured on a scale of 1-5 where 1 is the most resistant and 5 is the least resistant.

Clearfield herbicide trait. Protects crops from a family of herbicides by genetically inhibiting the activity of the enzyme, acetolactate synthase (ALS).

Typical commercial processing. As referred to herein, typically commercial processing means the refining, bleaching, and deodorizing of a canola oil which renders it suitable for the application in which it is intended. Examples of typical commercial processing can be found in, for example, *CANOLA AND RAPESEED PRODUCTION, CHEMISTRY NUTRITION AND PROCESSING TECHNOLOGY*, edited by Fereidoon Shahidi, published by Van Nostrand Reinhold (1990).

Cotyledon width. The cotyledons are leaf structures that form in the developing seeds of canola which make up the majority of the mature seed of these species. When the seed germinates, the cotyledons are pushed out of the soil by the growing hypocotyls (segment of the seedling stem below the cotyledons and above the root) and they unfold as the first photosynthetic leafs of the plant. The width of the cotyledons varies by variety and can be classified as narrow, medium, or wide.

Elite canola. A canola cultivar which has been stabilized for certain commercially important agronomic traits comprising a stabilized yield of about 100% or greater relative to the yield of check varieties in the same growing location growing at the same time and under the same conditions. In one embodiment, "elite canola" means a canola cultivar stabilized for certain commercially important agronomic traits comprising a stabilized yield of 110% or greater relative to the yield of check varieties in the same growing location growing at the same time and under the same conditions. In another embodiment, "elite canola" means a canola cultivar stabilized for certain commercially important agronomic traits comprising a stabilized yield of 115% or greater relative to the yield of check varieties in the same growing location growing at the same time and under the same conditions.

Elite canola cultivar. A canola cultivar, per se, which has been sold commercially.

Elite canola parent cultivar. A canola cultivar which is the parent cultivar of a canola hybrid that has been commercially sold.

Embryo. The embryo is the small plant contained within a mature seed.

FAME analysis. Fatty Acid Methyl Ester analysis is a method that allows for accurate quantification of the fatty acids that make up complex lipid classes.

Flower bud location. The location of the unopened flower buds relative to the adjacent opened flowers is useful in distinguishing between the canola species. The unopened buds are held above the most recently opened flowers in *B. napus* and they are positioned below the most recently opened flower buds in *B. rapa*.

Flowering date or date to flower. This is measured by the number of days from planting to the stage when 50% of the plants in a population have one or more open flowers. This varies from variety to variety.

Glucosinolates. These are measured in micromoles (μm) of total alipathic glucosinolates per gram of air-dried oil-free meal. The level of glucosinolates is somewhat influenced by the sulfur fertility of the soil, but is also controlled by the genetic makeup of each variety and thus can be useful in characterizing varieties.

Growth habit. At the end of flowering, the angle relative to the ground surface of the outermost fully expanded leaf petioles is a variety specific trait. This trait can range from erect (very upright along the stem) to prostrate (almost horizontal and parallel with the ground surface).

Imidazolinone resistance (Imi). Resistance and/or tolerance is conferred by one or more genes which alter acetolactate synthase (ALS), also known as acetohydroxy acid synthase (AHAS) allowing the enzyme to resist the action of imidazoline.

Leaf attachment to the stem. This trait is especially useful for distinguishing between the two canola species. The base of the leaf blade of the upper stem leaves of *B. rapa* completely clasp the stem whereas those of the *B. napus* only partially clasp the stem. Those of the mustard species do not clasp the stem at all.

Leaf blade color. The color of the leaf blades is variety specific and can range from light to medium dark green to blue green.

Leaf development of lobes. The leaves on the upper portion of the stem can show varying degrees of development of lobes which are disconnected from one another along the petiole of the leaf. The degree of lobing is variety specific and can range from absent (no lobes)/weak through very strong (abundant lobes).

Leaf glaucosity. This refers to the waxiness of the leaves and is characteristic of specific varieties although environment can have some effect on the degree of waxiness. This trait can range from absent (no waxiness)/weak through very strong. The degree of waxiness can be best determined by rubbing the leaf surface and noting the degree of wax present.

Leaf indentation of margin. The leaves on the upper portion of the stem can also show varying degrees of serration along the leaf margins. The degree of serration or indentation of the leaf margins can vary from absent (smooth margin)/weak to strong (heavy saw-tooth like margin).

Leaf pubescence. The leaf pubescence is the degree of hairiness of the leaf surface and is especially useful for distinguishing between the canola species. There are two main classes of pubescence which are glabrous (smooth/not hairy) and pubescent (hairy) which mainly differentiate between the *B. napus* and *B. rapa* species, respectively.

Leaf surface. The leaf surface can also be used to distinguish between varieties. The surface can be smooth or rugose (lumpy) with varying degrees between the two extremes.

Percent linolenic acid. Percent oil of the seed that is linolenic acid.

Maturity or Date to Maturity. The maturity of a variety is measured as the number of days between planting and physiological maturity. This is a useful trait in distinguishing varieties relative to one another.

Oil content. This is measured as percent of the whole dried seed and is characteristic of different varieties. It can be determined using various analytical techniques such as NMR, NIR, and Soxhlet extraction.

Percent oleic acid (OLE). Percent oil of the seed that is oleic acid.

Percentage of total fatty acids. This is determined by extracting a sample of oil from seed, producing the methyl esters of fatty acids present in that oil sample and analyzing the proportions of the various fatty acids in the sample using gas chromatography. The fatty acid composition can also be a distinguishing characteristic of a variety.

Petal color. The petal color on the first day a flower opens can be a distinguishing characteristic for a variety. It can be white, varying shades of yellow or orange.

Plant height. This is the height of the plant at the end of flowering if the floral branches are extended upright (i.e., not lodged). This varies from variety to variety and although it can be influenced by environment, relative comparisons between varieties grown side by side are useful for variety identification.

Protein content. This is measured as percent of whole dried seed and is characteristic of different varieties. This can be determined using various analytical techniques such as NIR and Kjeldahl.

Resistance to lodging. This measures the ability of a variety to stand up in the field under high yield conditions and severe environmental factors. A variety can have good (remains upright), fair, or poor (falls over) resistance to lodging. The degree of resistance to lodging is not expressed under all conditions but is most meaningful when there is some degree of lodging in a field trial.

Seed coat color. The color of the seed coat can be variety specific and can range from black through brown through yellow. Color can also be mixed for some varieties.

Seed coat mucilage. This is useful for differentiating between the two species of canola with *B. rapa* varieties having mucilage present in their seed coats whereas *B. napus* varieties do not have this present. It is detected by imbibing seeds with water and monitoring the mucilage that is exuded by the seed.

Seedling growth habit. The rosette consists of the first 2-8 true leaves and a variety can be characterized as having a strong rosette (closely packed leaves) or a weak rosette (loosely arranged leaves).

Single Gene Converted (Conversion). Single gene converted (conversion) plant refers to plants which are developed by a plant breeding technique called backcrossing, or via genetic engineering, wherein essentially all of the desired morphological and physiological characteristics of a variety are recovered in addition to the single gene transferred into the variety via the backcrossing technique or via genetic engineering.

Stabilized. Reproducibly passed from one generation to the next generation of inbred plants of same variety.

Stem intensity of anthocyanin coloration. The stems and other organs of canola plants can have varying degrees of purple coloration which is due to the presence of anthocyanin (purple) pigments. The degree of coloration is somewhat subject to growing conditions, but varieties typically show varying degrees of coloration ranging from: absent (no purple)/very weak to very strong (deep purple coloration).

Total Saturated (TOTSAT). Total percent oil of the seed of the saturated fats in the oil including C12:0, C14:0, C16:0, C18:0, C20:0, C22:0 and C24.0.

Mean Yield. Mean yield of all canola entries grown at a given location.

Yield. Greater than 10% above the mean yield across 10 or more locations.

Check Average. Average for one or more checks in a given location.

DN040244 was developed from the cross of DN011520 (Nex 822CL) and DN995820 through traditional plant breeding and the dihaploid methodology. Canola cultivar DN040244 is stable and uniform after three generations following dihaploid production and chromosome doubling and no off-type plants have been exhibited in evaluation.

DN040244 is a high oleic, low linolenic acid canola cultivar that is resistant to blackleg, possessed Clearfield herbicide trait, Natreon oil profile, high protein, low glucosinolates, Fusarium wilt and White Rust tolerance. Additionally, DN040244 has genes conferring tolerance to one or more herbicides including, but not limited to: imidazolinone, sulfonylurea, glyphosate, glufosinate, L-phosphinothricin, triazine, Clearfield, Dicamaba, 2,4-D, pyridyloxy auxin, fenoxaprop-p-ethyl ("fop"), cyclohexanedione ("dim") and benzonitrile, and related herbicide families and/or groups of any thereof. In a particular embodiment, herbicide resistance in DN040244 is Round-up Ready™ glypohsate resistance resulting from the introgression of MON event GT-73.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The cultivar has been increased with continued observation for uniformity.

This invention is also directed to methods for producing a canola plant by crossing a first parent canola plant with a second parent canola plant, wherein the first or second canola plant is the canola plant from the cultivar DN040244. Further, both first and second parent canola plants may be from the cultivar DN040244. Therefore, any methods using the cultivar DN040244 are part of this invention: selfing, backcrosses, hybrid breeding, and crosses to populations. Any plants produced using cultivar DN040244 as parents are within the scope of this invention.

Useful methods include, but are not limited to, expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device *Agrobacterium*-mediated transformation. Transformant plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed variety or cultivar.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed canola plants, using transformation methods as described below to incorporate transgenes into the genetic material of the canola plant(s).

Expression Vectors for Canola Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene under the control of plant regulatory signals which confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985); Gordon-Kamm et al., *Plant Cell* 2:603-618 (1990); and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987); Shah et al., *Science* 233:478 (1986); Charest et al., *Plant Cell Rep.* 8:643 (1990).

Another class of marker genes for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987); Teeri et al., *EMBO J.* 8:343 (1989); Koncz et al., *Proc. Natl. Acad. Sci. U.S.A.* 84:131 (1987); DeBlock et al., *EMBO J.* 3:1681 (1984).

Recently, in vivo methods for visualizing GUS activity that do not require destruction of plant tissue have been made available. Molecular Probes publication 2908, *Imagene Green™*, p. 1-4 (1993); and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GEP) has been utilized as a marker for gene expression in prokaryotic and eukaryotic cells. Chalfie et al., *Science* 263: 802 (1994). GFP and mutants of GFP may be used as screenable markers.

Expression Vectors for Canola Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in canola. Optionally, the inducible promoter is operably linked to a nucleotide sequence encoding a signal sequence which is operably linked to a gene for expression in canola. With an inducible promoter, the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. en Genetics* 227:229-237 (1991); and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in canola or the constitutive promoter is operably linked to a nucleotide sequence encoding a signal sequence which is operably linked to a gene for expression in canola.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989); and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992); and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter is operably linked to a gene for expression in canola. Optionally, the tissue-specific promoter is operably linked to a nucleotide sequence encoding a signal sequence which is operably linked to a gene for expression in canola. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983); and Sengupta-Gopalan et al., *Proc. Natl. Acad. Sci. U.S.A.* 82-3320-3324 (1985)); a leaf-specific and light-induced promoter such as that from cab or rubisco (Simpson et al., *EMBO J.* 4(11): 2723-2729 (1985); and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 24:161-168 (1993)) or a microspore-preferred promoter such as that from apg (Twell et al., *Sex. Plant Reprod.* 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment, or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al. *Plant J.* 2:129 (1991); Kalderon, et al., A short amino acid sequence able to specify nuclear location, *Cell* 39:499-509 (1984); Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a canola plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* alpha.-amylase inhibitor); and U.S. Pat. No. 5,494,813 (Hepher and Atkinson, issued Feb. 27, 1996).

G. An insect-specific hormone or pheromone such as an ecdysteroid or juvenile hormone, a variant thereof a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor); and Pratt et al., Biochem. Biophys. Res. Comm. 163:1243 (1989) (an allostatin is identified in Diploptera puntata). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci. 89:43 (1993), of heterologous expression of a cecropin-.beta., lytic peptide analog to render transgenic tobacco plants resistant to Pseudomonas solanacearum.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from Streptomyces species, including Streptomyces hygroscopicus and Streptomyces viridichromogenes), and pyridinoxy or phenoxy proprionic acids and cyclohexones (AC-Case inhibitor-encoding genes), See, for example, U.S. Pat. No. 4,940,835 to Shah, et al. and U.S. Pat. No. 6,248,876 to Barry et. al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al., DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., Theor. Appl. Genet. 83:435 (1992). GAT genes capable of conferring glyphosate resistance are described in WO 2005012515 to Castle et. al. Genes conferring resistance to 2,4-D, fop and pyridyloxy auxin herbicides are described in WO 2005107437 and U.S. patent application Ser. No. 11/587, 893, both assigned to Dow AgroSciences LLC.

C. An herbicide that inhibits photosynthesis, such as a triazine (psbA and gs+ genes) or a benzonitrile (nitrilase gene). Przbila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Sogaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Canola Transformation

Numerous methods for plant transformation have been developed including biological and physical plant transformation protocols. See, for example, Miki et al., "procedures for Introducing Foreign DNA into Plants" in *Methods in Plant Molecular Biology and Biotechnology*, Glick B, R. and Thompson, I. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., *EMBO J*, 4:2731 (1985), Christou et al., *Proc. Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of canola target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular canola cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Canolas

Further production of the DN040244 cultivar can occur by self-pollination or by tissue culture and regeneration. Tissue culture of various tissues of canola and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," *Plant Cell Reports* 4:4-6 (1985); Barsby, T. L., et al., "A Rapid and Efficient Alternative Procedure for the Regeneration of Plants from Hypocotyl Protoplasts of *Brassica napus,*" *Plant Cell Reports* (Spring, 1996); Kartha, K., et al., "in vitro Plant Formation from Stem Explants of Rape," *Physiol. Plant,*

31:217-220 (1974); Narasimhulu, S., et al., "Species Specific Shoot Regeneration Response of Cotyledonary Explants of Brassicas," *Plant Cell Reports* (Spring 1988); Swanson, E., "Microspore Culture in *Brassica*," *Methods in Molecular Biology*, Vol. 6, Chapter 17, p. 159 (1990).

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," *Crop Sci.* 31:333-337 (1991); Stephens, P. A., et al., "Agronomic Evaluation of Tissue-Culture-Derived Soybean Plants," *Theor. Appl. Genet.* (1991) 82:633-635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," *Plant Cell, Tissue and Organ Culture*, 28:103-113 (1992); Dhir, S. et al., "Regeneration of Fertile Plants from Protoplasts of Soybean (*Glycine max* L. Merr.); Genotypic Differences in Culture Response," *Plant Cell Reports* (1992) 11:285-289; Pandey, P. et al., "Plant Regeneration from Leaf and Hypocotyl Explants of *Glycine-wightii* (W. and A.) VERDC. var. *longicauda*," *Japan J. Breed.* 42:1-5 (1992); and Shetty, K., et al., "Stimulation of In Vitro Shoot Organogenesis in *Glycine max* (Merrill.) by Allantoin and Amides," *Plant Science* 81:245-251 (1992). The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference. Thus, another aspect of this invention is to provide cells which upon growth and differentiation produce canola plants having the physiological and morphological characteristics of canola variety DN040244.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, describe certain techniques, the disclosures of which are incorporated herein by reference.

Single-Gene Converted (Conversion) Plants

When the term "canola plant" is used in the context of the present invention, this also includes any single gene conversions of that variety. The term "single gene converted plant" as used herein refers to those canola plants which are developed by a plant breeding technique called backcrossing, or via genetic engineering, wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental canola plant which contributes the gene for the desired characteristic is termed the "nonrecurrent" or "donor parent." This terminology refers to the fact that the nonrecurrent parent is used one time in the backcross protocol and therefore does not recur. The parental canola plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,97745, the disclosures of which are specifically hereby incorporated by reference.

This invention also is directed to methods for producing a canola plant by crossing a first parent canola plant with a second parent canola plant wherein the first or second parent canola plant is a canola plant of the variety DN040244. Further, both first and second parent canola plants can come from the canola variety DN040244. Thus, any such methods using the canola variety DN040244 are part of this invention: selfing, backcrosses, hybrid production, crosses to populations, and the like. All plants produced using canola variety DN040244 as a parent are within the scope of this invention, including those developed from varieties derived from canola variety DN040244. Advantageously, the canola variety could be used in crosses with other, different, canola plants to produce first generation (F.sub.1) canola hybrid seeds and plants with superior characteristics. The variety of the invention can also be used for transformation where exogenous genes are introduced and expressed by the variety of the invention. Genetic variants created either through traditional breeding methods using variety DN040244 or through transformation of DN040244 by any of a number of protocols known to those of skill in the art are intended to be within the scope of this invention.

The invention is also directed to Canola meal from seeds of an elite canola variety. In a particular embodiment, the seeds comprise at least 45% protein by weight. Canola meal of the present invention preferably has low fiber content, higher protein, and lower glucosinolate levels compared to presently used canola meal.

Oxidative Stability

Stability can be defined as the resistance of a vegetable oil to oxidation and to the resulting deterioration due to the generation of products causing rancidity and decreasing food quality. Tests for oxidative stability attempt to accelerate the normal oxidation process to yield results that can be translated into quality parameters for different food ails and to predict their shelf lives. Stability methods are also useful to evaluate antioxidants and their effects on protection of foods against lipid oxidation.

Lipid oxidation in food products develops slowly initially, and then accelerates at later stages during storage. The induction period is defined as the time to reach a constant percent oxidation of the fat as related to the end of shelf life. The induction period is measured either as the time required for a sudden change in rate of oxidation, or by estimating the intersection point between the initial and final rates of oxidation. For vegetable oils containing linoleic and linolenic acid, such as soybean and canola oils, the end-points for acceptability will occur at relatively low levels of oxidation (peroxide values between 1 and 10 Meq/kg).

Factors Affecting Oxidative Stability

The difference in stability between different vegetable oils is due to their different fatty acid profiles, the effect of processing, initial levels of oxidation at the start of the storage period, and other factors including, minor components, including the presence of metal impurities, formulation, packaging and environmental storage conditions. From the crude stage to different stages of processing of vegetable oils, some oxidation can take place that will affect the subsequent oxidative stability of the final oil product during storage.

Oxidative Stability Methods

To estimate the oxidative stability of a fat to oxidation, the sample is subjected to an accelerated oxidation test under standardized conditions and a suitable end-point is chosen to determine the level of oxidative deterioration. Methods involving elevated temperatures include:

1. Schaal Oven Test

The sample is heated at 50 to 60° C. until it reaches a suitable end-point based on peroxide value or carbonyl value such as the anisidine value. The results of this test correlate best with actual shelf life because the peroxide value end-point of 10 represents a relatively low degree of oxidation. See, limiting peroxide value in section D below.

2. Active Oxygen Method (AOM), Rancimat and Oxidation Stability Index (OSI). See, e.g., U.S. Pat. No. 5,339,294 to Matlock et. al. AOCS Method 12b-92, and Laubli, M. W. and Bruttel, P. A., JOACS 63:792-795 (1986).

Air is bubbled through a sample of oil in special test tubes heated at 98-100° C. and the progress of oxidation is followed by peroxide value determination in the AOM test, and by conductivity measurements in the Rancimat and OSI tests. The automated Rancimat and OSI tests may be run at temperatures ranging from 100-140° C., and the effluent gases are led through a vessel containing deionized water and the increase in conductivity measured are due to the formation of volatile organic acids (mainly formic acid) by thermal oxidation. The OSI is defined as the time point in hours of maximum change of the rate of oxidation based on conductivity.

D. Methods to Determine Oxidation

The peroxide value of oils is a measure of oxidation that is useful for samples that are oxidized to relatively low levels (peroxide values of less than 50), and under conditions sufficiently mild so that the hydroperoxides, which are the primary products formed by oxidation, are not markedly decomposed. A limiting peroxide value of 10 meq/kg was specified for refined oils by FAQ/WHO standards (Joint FAQ/WHO Food Standard Program Codex Alimentarius Commission, Report of 16th session of Committee on Fats and Oils, London, 1999).

The anisidine test measures high molecular weight saturated and unsaturated carbonyl compounds in oils. The test provides useful information on non-volatile carbonyl compounds formed in oils during processing of oils containing linolenate (soybean and rapeseed). The Totox value (anisidine value+2 times peroxide value) is used as an empirical measure of the precursor non-volatile carbonyl compounds present in processed oils plus any further oxidation products developed after storage.

Tables

Table 1 shows the mean agronomic and quality data of DN040244 relative to check variety Nex 830 CL, Nex 705, and Nex 715 in 2004. In the table, column 1 shows the variety, columns 2 and 3 show the date to flower (DTF) and the date to maturity (DTM). Column 4 shows the lodging score (LDG) lodging score based on a range of 1-5, with 1 being good (upright plants) and 5 being poor (plant fallen over). Columns 5 and 6 show late season vigor as rated by two different observers (LSV 1 and LSV 2). Columns 7 and 8 show crop injury (as assessed by two observers, respectively) (CI 1 and CI 2) after herbicide application. Columns 9 through 12 show percent of C18:1, C18:2, C18:3, and C22:1. Column 13 shows the percent total saturated fatty acids (% Sats). Column 14 shows the Oil content (% Oil), column 15 shows the Protein (% Meal Protein), and columns 16 and 17 show the total glucosinolates (µmol/g seed) as measured using near infrared (Glucs-NIR) and wet chemistry (Glucs-WC) methods. Column 18 shows Fusarium wilt tolerance (GH FW) and column 19 shows White Rust tolerance (White Rust).

Table 2 shows the mean agronomic and quality characteristics of DN040244 versus industry standard check varieties (Q2 and 46A65) and check varieties Hex 830 CL, Nex 828 CL, and Nex 705) varieties in 2004-2005. In the table, column 1 shows the variety, columns 2 and 3 show the date to maturity (DTM) and the date to flower (DTF). Column 4 shows the height (HT). Columns 5 and 6 show the late season vigor as rated by two different observers (LSV-CC and LSV-ST). Column 7 shows the mean yield in kilograms per hectare (Yield (kg/ha)). Columns 8 through 11 show the yield as compared to various variety yields (Q2+45A65, Nex 830, Nex 705, and 46A76). Columns 12 through 15 show percent of C18:1, C18:2, C18:3, and C22:1. Column 16 shows the percent total saturated fatty acids (% Sats). Column 17 shows the Oil content (Oil), column 18 shows the Protein (Protein), and column 19 shows the total glucosinolates (µmol/g seed). The data demonstrate, inter alia, the combination of Natreon oil quality with significantly higher yield.

Table 3 shows agronomic and quality traits of DN040244 and other Nexera lines versus industry standard check varieties (Q2 and 46A65, 5020 CL) and check Hex 830 CL) variety in 2005. In the table, column 1 shows the variety. Columns 2 and 3 show crop injury 11 and 12 days (CH-Ody and C12-Ody), respectively, after application of Odyssey herbicide (an imi herbicide). Columns 4 and 5 show crop injury 11 and 12 days (CH-Bey and C12-Bey), respectively, after application of Beyond herbicide. Column 6 shows early season vigor (ESV). Columns 7 and 8 show the date to flower (DTF) and the date to maturity (DTM). Column 9 shows height (HGT), column 10 shows the lodging score (LDG) lodging score, and column 11 shows the mean yield in kilograms per hectare (Yield (kg/ha)). Columns 12 through 14 show the yield as compared to various variety yields (YAPO Q2+45A65, 5020 CL, and Nex 830 CL). Column 15 shows Blackleg disease ratings are based on a 1-5 scale with 1 being resistant and 5 being susceptible. Column 16 shows a yield as a percent of the Westar check variety (% of Westar). Column 17 shows the tolerance of DN040244 to Blackleg disease (*Leptosphaeria maculans*) ((Blackleg). Column 18 shows Fusarium wilt tolerance (FW-Fld). Columns 19 through 22 show percent of C18:1, C18:2, C18:3, and C22:1. Column 23 shows the percent total saturated fatty acids (% Sats). Column 24 shows the Oil content (% Oil DM), column 25 shows the Protein (% Meal Protein), and column 26 shows the total glucosinolates (µmol/g seed) (Tot Gluc). Column 27 shows the chlorophyll content (Chlorophyll) and column 28 shows the green seed content (Green See (3 Loc)). The data confirms the Natreon oil profile, high oil and protein, higher yield, in combination with low chlorophyll Blackleg resistance, Fusarium wilt resistance and White Rust tolerance.

Deposit Information

A deposit of the Dow AgroSciences proprietary canola cultivar DN040244 disclosed above and recited in the appended claims has been made with the American Type Culture Collection (ATCC), 10801 University Boulevard, Manassas, Va. 20110. The date of deposit was Jun. 25, 2009. All restrictions upon the deposit have been removed, and the deposit is intended to meet all of the requirements of 37 C.F.R. Sections 1.801-1.809. The ATCC accession number is PTA-9289. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

TABLE 1

| Name | DTF | DTM | LDG | LSV 2 | LSV 1 | CI 1 | CI 2 | C18:1 | C18:2 | C18:3 |
|---|---|---|---|---|---|---|---|---|---|---|
| Nex 705 | 57 | 114 | 2.75 | 3.75 | 4.75 | 30.00 | 70.00 | 72.59 | 16.36 | 2.52 |
| Nex 715 | 52 | 108 | 3.25 | 4.00 | 5.00 | 30.00 | 70.00 | 71.84 | 16.07 | 3.32 |
| Nex 830 CL | 55 | 115 | 2.82 | 2.73 | 2.55 | 4.73 | 5.18 | 71.43 | 18.08 | 1.93 |
| DN040241 | 52 | 107 | 2.50 | 3.00 | 3.00 | 9.50 | 6.50 | 72.83 | 16.36 | 2.07 |
| DN040244 | 52 | 104 | 2.50 | 2.00 | 3.00 | 7.50 | 5.00 | 73.56 | 15.46 | 2.06 |
| Nex 705 | 57 | 116 | 3.00 | 3.75 | 3.00 | 30.00 | 70.00 | 72.40 | 16.85 | 2.35 |
| Nex 715 | 53 | 107 | 2.53 | 3.06 | 3.16 | 13.16 | 22.78 | 72.35 | 16.43 | 2.28 |
| Nex 830 CL | 54 | 115 | 2.47 | 2.07 | 2.07 | 5.80 | 5.27 | 71.32 | 18.16 | 2.03 |
| DN040839 | 53 | 104 | 2.00 | 2.00 | 3.00 | 7.00 | 5.00 | 73.70 | 15.51 | 2.11 |
| DN040844 | 53 | 110 | 2.00 | 3.00 | 2.50 | 5.00 | 5.00 | 73.52 | 15.94 | 2.09 |
| DN040845 | 53 | 106 | 2.00 | 2.50 | 3.00 | 6.50 | 5.00 | 75.64 | 13.66 | 1.94 |
| DN040847 | 55 | 105 | 2.00 | 2.00 | 2.50 | 9.50 | 6.50 | 73.35 | 15.86 | 2.03 |
| DN040856 | 55 | 110 | 2.00 | 2.50 | 3.00 | 7.50 | 7.50 | 73.75 | 15.62 | 2.19 |
| Nex 705 | 55 | 113 | 3.00 | 4.00 | 4.00 | 30.00 | 70.00 | 72.79 | 16.23 | 2.85 |
| Nex 715 | 51 | 105 | 2.75 | 3.67 | 4.50 | 30.00 | 70.00 | 74.16 | 14.71 | 2.79 |
| Nex 830 CL | 55 | 114 | 2.38 | 2.46 | 2.62 | 6.23 | 5.31 | 72.14 | 17.67 | 1.95 |
| DN041100 | 54 | 110 | 2.00 | 3.00 | 3.50 | 7.00 | 7.50 | 74.63 | 15.12 | 2.10 |
| Nex 705 | 55 | 113 | 2.80 | 3.70 | 4.00 | 30.00 | 70.40 | 72.09 | 15.90 | 2.92 |
| Nex 715 | 51 | 105 | 3.00 | 3.63 | 4.25 | 30.00 | 70.00 | 73.74 | 14.56 | 3.04 |
| Nex 830 CL | 55 | 113 | 2.53 | 2.38 | 2.56 | 5.76 | 5.26 | 71.16 | 18.28 | 2.08 |

| Name | C22:1 | % Sats | % Oil DM | % Meal Protein DM | Glucs-NIR | Glucs-WC | GH FW | White Rust |
|---|---|---|---|---|---|---|---|---|
| Nex 705 | 0.03 | 5.66 | 52.82 | 45.45 | 13.20 | 5.30 | | |
| Nex 715 | 0.01 | 6.02 | 46.41 | 42.93 | 10.03 | 7.30 | | |
| Nex 830 CL | 0.03 | 5.52 | 51.65 | 46.11 | 8.43 | 4.80 | | |
| DN040241 | 0.03 | 5.63 | 50.33 | 44.15 | 10.57 | 9.00 | R | R |
| DN040244 | 0.02 | 6.30 | 50.30 | 45.00 | 10.73 | 11.90 | R | R |
| Nex 705 | 0.02 | 5.59 | 51.38 | 45.15 | 14.82 | | | |
| Nex 715 | 0.02 | 5.85 | 48.22 | 43.42 | 10.49 | 7.30 | | |
| Nex 830 CL | 0.01 | 5.47 | 51.67 | 45.86 | 8.87 | | | |
| DN040839 | 0.02 | 5.89 | 51.23 | 46.65 | 10.75 | 6.10 | R | R |
| DN040844 | 0.01 | 5.85 | 51.02 | 44.00 | 10.96 | 9.60 | R | R |
| DN040845 | 0.01 | 5.85 | 51.67 | 43.95 | 11.66 | 11.80 | R | R |
| DN040847 | 0.01 | 6.13 | 50.17 | 44.50 | 7.84 | 8.10 | R | R |
| DN040856 | 0.01 | 5.63 | 51.96 | 43.80 | 11.21 | 6.90 | R | R |
| Nex 705 | 0.03 | 5.43 | 52.01 | 44.18 | 12.01 | | | |
| Nex 715 | 0.02 | 5.72 | 46.22 | 42.13 | 9.91 | 7.50 | | |
| Nex 830 CL | 0.01 | 5.31 | 51.48 | 45.23 | 8.85 | 4.40 | | |
| DN041100 | 0.01 | 5.10 | 51.13 | 44.45 | 12.82 | 11.70 | R | R |
| Nex 705 | 0.45 | 5.49 | 50.31 | 43.61 | 13.58 | 14.30 | | |
| Nex 715 | 0.01 | 5.90 | 45.43 | 41.84 | 10.06 | | | |
| Nex 830 CL | 0.01 | 5.33 | 49.88 | 44.52 | 9.00 | 5.20 | | |

TABLE 2

| Name | DTM | DTF | HT | LSV-CC | LSV-ST | Yield (kg/ha) | Q2 + 45A65 | Nex 830 | Nex 705 |
|---|---|---|---|---|---|---|---|---|---|
| DN040241 | 95 | 47 | 92 | 2.67 | 2.50 | 2235 | 100 | 90 | 112 |
| DN040244 | 94 | 48 | 88 | 2.67 | 3.33 | 2133 | 96 | 86 | 107 |
| DN040839 | 95 | 47 | 97 | 2.33 | 3.17 | 2670 | 120 | 108 | 134 |
| DN040844 | 96 | 46 | 95 | 3.33 | 3.00 | 2498 | 112 | 101 | 125 |
| DN040845 | 92 | 45 | 93 | 2.33 | 2.50 | 2642 | 118 | 107 | 133 |
| DN040847 | 93 | 47 | 87 | 3.00 | 2.67 | 2291 | 103 | 92 | 115 |
| DN040856 | 95 | 48 | 88 | 3.00 | 2.83 | 2419 | 108 | 98 | 121 |
| DN041100 | 96 | 47 | 92 | 3.00 | 3.17 | 2102 | 94 | 85 | 106 |
| 46A65 | 87 | 45 | 78 | 3.67 | 3.33 | 2220 | 99 | 90 | 111 |
| 46A76 | 98 | 49 | 102 | 3.33 | 3.04 | 2181 | 98 | 88 | 109 |
| Nex 828 CL | 96 | 47 | 96 | 2.83 | 2.17 | 2484 | 111 | 100 | 125 |
| Lolinda | 95 | 50 | 88 | 4.00 | 2.83 | 1667 | 75 | 67 | 84 |
| Nex 705 | 93 | 49 | 83 | 3.00 | 2.17 | 1992 | 89 | 80 | 100 |
| Nex 715 | 93 | 50 | 83 | 4.00 | 2.91 | 1867 | 84 | 75 | 94 |
| Nex 830 CL | 97 | 47 | 99 | 2.98 | 2.83 | 2479 | 111 | 100 | 124 |
| Q2 | 87 | 45 | 90 | 2.33 |  | 2246 | 101 | 91 | 113 |

| Name | 46A76 | C18:1 | C18:2 | C18:3 | C22:1 | % Sats | Oil | Protein | Glucs |
|---|---|---|---|---|---|---|---|---|---|
| DN040241 | 102 | 75.78 | 13.70 | 1.68 | 0.01 | 6.21 | 46.52 | 47.23 | 7.37 |
| DN040244 | 98 | 76.19 | 13.27 | 1.47 | 0.01 | 6.65 | 46.44 | 49.31 | 3.00 |
| DN040839 | 122 | 74.53 | 14.31 | 1.85 | 0.00 | 6.74 | 45.54 | 49.67 | 1.80 |
| DN040844 | 115 | 76.15 | 13.47 | 1.48 | 0.01 | 6.52 | 46.58 | 48.51 | 3.50 |
| DN040845 | 121 | 76.80 | 12.77 | 1.66 | 0.02 | 6.43 | 47.25 | 48.36 | 6.40 |
| DN040847 | 105 | 74.81 | 14.20 | 1.68 | 0.02 | 6.86 | 44.93 | 48.15 | 3.33 |
| DN040856 | 111 | 76.93 | 12.94 | 1.60 | 0.01 | 6.22 | 46.02 | 46.84 | 5.64 |
| DN041100 | 96 | 77.50 | 12.49 | 1.70 | 0.01 | 5.86 | 47.09 | 48.12 | 11.21 |
| 46A65 | 102 | 65.09 | 19.10 | 6.76 | 0.02 | 6.69 | 44.97 | 45.12 | 14.11 |
| 46A76 | 100 | 65.03 | 17.47 | 7.94 | — | 7.00 | 44.13 | 45.63 | 10.27 |
| Nex 828 CL | 114 | 73.19 | 16.47 | 1.60 | 0.02 | 6.08 | 45.60 | 48.11 | 5.37 |
| Lolinda | 76 | 65.47 | 23.98 | 2.21 | 0.02 | 6.15 | 42.46 | 44.46 | 11.76 |
| Nex 705 | 91 | 77.31 | 13.09 | 1.43 | 0.02 | 5.95 | 48.58 | 47.26 | 8.01 |
| Nex 715 | 86 | 76.92 | 13.04 | 1.62 | 0.02 | 6.09 | 43.14 | 46.33 | 9.66 |
| Nex 830 CL | 114 | 73.38 | 16.32 | 1.54 | 0.01 | 6.09 | 46.36 | 48.56 | 5.85 |
| Q2 | 103 | 65.33 | 18.08 | 7.38 | 0.09 | 6.76 | 43.73 | 46.46 | 7.53 |

TABLE 3

| Candidate line/Check | DTF | HGT (cm) | LDG (1-5) | Yield (Kg/Ha) | YAPO 46A65 + Q2 | YAPO 5020 | YAPO Nex 830 CL | Rating | % of Westar |
|---|---|---|---|---|---|---|---|---|---|
| 5020 | 43 | 98 | 99 | 2.50 | 3454 | 124 | 100 | 116 |  |  |
| 45A65 | 44 | 102 | 99 | 2.75 | 2786 | 101 | 81 | 94 |  |  |
| DN040241 | 46 | 105 | 98 | 2.30 | 2782 | 101 | 81 | 93 | 1.14 | 42 |
| DN040244 | 45 | 103 | 97 | 2.86 | 2731 | 99 | 79 | 92 | 0.95 | 35 |
| DN040839 | 46 | 104 | 98 | 2.16 | 2731 | 99 | 79 | 92 | 1.30 | 48 |
| DN040844 | 45 | 105 | 100 | 2.14 | 2653 | 97 | 77 | 89 | 0.82 | 30 |
| DN040845 | 45 | 105 | 99 | 2.25 | 2861 | 105 | 83 | 96 | 1.28 | 47 |
| DN040847 | 46 | 106 | 98 | 1.79 | 2623 | 96 | 76 | 88 | 0.64 | 23 |
| DN040856 | 46 | 105 | 97 | 2.25 | 2742 | 99 | 79 | 92 | 0.99 | 36 |
| DN041100 | 46 | 105 | 94 | 2.11 | 2468 | 91 | 71 | 83 | 1.18 | 43 |
| Nex 830 CL | 46 | 106 | 108 | 2.48 | 2976 | 108 | 86 | 100 |  |  |
| Q2 | 45 | 102 | 99 | 2.51 | 2756 | 99 | 80 | 93 |  |  |
| 45A71 | — | — | — | — | — | — | — | — |  |  |
| PM2 | — | 2.82 | — | — | — | — | — | — |  |  |
|  |  | 1.79 |  |  |  |  |  |  |  |  |
| LSD (.05) | 0.8 | 104 | 11.0 | 0.7 | 411 |  |  |  |  |  |
| CV (SAS) | 8.7 |  | 10.6 | 13.5 | 12.2 |  |  |  |  |  |
| Mean | 45 |  | 97 | 2 | 2656 |  |  |  |  |  |
| ACExcel |  |  |  |  |  |  |  |  | 1.50 | 55 |
| Defender |  |  |  |  |  |  |  |  | 1.65 | 60 |
| Q2 |  |  |  |  |  |  |  |  | 1.00 | 36 |
| Westar |  |  |  |  |  |  |  |  | 2.74 | 100 |

| Candidate line/Check | Blackleg | FW-Fld | C18:1 | C18:2 | C18:3 | C22:1 | % Sats | % Oil DM | % Meal Protein DM | Tot Gluc | Chlorophyll | Green Seed (3 Loc) |
|---|---|---|---|---|---|---|---|---|---|---|---|---|
| 5020 |  |  | 62.95 | 18.23 | 9.40 | 0.01 | 6.9 | 50.1 | 45.5 | 12.5 | 7.9 | 0.60 |
| 45A65 |  |  | 62.21 | 19.75 | 8.65 | 0.02 | 6.6 | 49.3 | 45.3 | 17.5 | 9.1 | 0.40 |
| DN040241 | MR | R | 71.16 | 16.79 | 2.40 | 0.02 | 6.4 | 49.8 | 46.8 | 11.6 | 14.7 | 2.00 |
| DN040244 | MR | R | 71.66 | 16.27 | 2.30 | 0.02 | 6.8 | 49.5 | 47.7 | 10.6 | 12.1 | 0.40 |

TABLE 3-continued

| | | | | | | | | | | | |
|---|---|---|---|---|---|---|---|---|---|---|---|
| DN040839 | MR | R | 71.06 | 16.66 | 2.21 | 0.02 | 6.7 | 49.4 | 48.4 | 8.1 | 16.2 | 0.30 |
| DN040844 | R | R | 72.60 | 15.94 | 2.18 | 0.01 | 6.6 | 51.3 | 48.5 | 11.9 | 11.7 | 0.90 |
| DN040845 | MR | R | 73.36 | 15.09 | 2.21 | 0.01 | 6.4 | 50.7 | 47.7 | 11.2 | 9.1 | 0.30 |
| DN040847 | R | R | 71.39 | 16.45 | 2.22 | 0.01 | 6.9 | 49.0 | 47.4 | 9.0 | 14.5 | 0.90 |
| DN040856 | MR | R | 72.44 | 15.93 | 2.31 | 0.02 | 6.4 | 50.6 | 47.5 | 11.0 | 14.9 | 0.40 |
| DN041100 | MR | R | 73.25 | 15.58 | 2.22 | 0.04 | 5.9 | 50.8 | 47.5 | 15.5 | 12.5 | 0.70 |
| Nex 830 CL | | | 69.36 | 18.89 | 2.22 | 0.01 | 6.4 | 49.1 | 46.9 | 8.4 | 17.6 | 2.00 |
| Q2 | | | 61.87 | 18.90 | 9.21 | 0.22 | 7.0 | 49.0 | 47.1 | 14.8 | 13.2 | 0.30 |
| 45A71 | | | — | — | — | — | — | — | — | — | — | — |
| PM2 | | | — | — | — | — | — | — | — | — | — | — |
| LSD (.05) | | | 2.90 | 1.22 | 1.18 | 0.14 | 0.6 | 2.4 | 1.2 | 2.3 | 12.1 | |
| CV (SAS) | | | 2.01 | 3.62 | 20.25 | 205.26 | 4.3 | 2.3 | 1.2 | 9.0 | 29.2 | |
| Mean | | | 70.55 | 16.82 | 2.97 | 0.03 | 6.5 | 49.4 | 46.7 | 12.9 | 34.4 | |
| ACExcel | MS | | | | | | | | | | | |
| Defender | MS | | | | | | | | | | | |
| Q2 | MR | | | | | | | | | | | |
| Westar | S | | | | | | | | | | | |

What is claimed is:

1. A seed of canola cultivar designated DN040244, wherein a representative sample of seed of said cultivar was deposited under ATCC Accession No. PTA-9289.

2. A canola plant, or a part thereof, produced by growing the seed of claim 1.

3. A method of introducing a desired trait into canola cultivar DN040244, wherein the method comprises: (a) crossing a DN040244 plant, wherein a representative sample of seed was deposited under ATCC Accession No. PTA-9289, with a plant of another canola cultivar that comprises a desired trait to produce $F_1$ progeny plants, wherein the desired trait is selected from the group consisting of male sterility, herbicide resistance, insect resistance, and resistance to bacterial disease, fungal disease or viral disease; (b) selecting one or more progeny plants that have the desired trait to produce selected progeny plants; (c) crossing the selected progeny plants with the DN040244 plants to produce backcross progeny plants; (d) selecting for backcross progeny plants that have the desired trait and physiological and morphological characteristics of canola cultivar DN040244 to produce selected backcross progeny plants; and (e) repeating steps (c) and (d) three or more times to produce selected fourth or higher backcross progeny plants that comprise the desired trait and an oleic acid value of about 70% and an α-linolenic acid value of less than about 3%.

4. The method of claim 3, wherein the plants further comprise a yield greater than about 2100 kg/ha, a protein value of greater than 45%, a glucosinolate value of less than 12%, or a chlorophyll value of less than 18%.

5. The method of claim 3, wherein the plants further comprise resistance to Blackleg (*Leptosphaeria maculans*), Fusarium wilt, or White Rust.

6. The method of claim 3, wherein the plants further comprise herbicide resistance to an herbicide selected from the group consisting of imidazolinone, sulfonylurea, glyphosate, glufosinate, L-phosphinothricin, triazine, Clearfield, Dicamaba, 2,4-D, and benzonitrile.

7. The method of claim 3, wherein the plants comprise all of the physiological and morphological characteristics of canola cultivar DN040244 as shown in Tables 1, 2 and 3.

8. A canola plant produced by the method of claim 3, wherein the plant has the desired trait and desired trait comprises an oleic acid value of about 70% and an α-linolenic acid value of less than about 3%.

9. The canola plant of claim 8, wherein the desired trait further comprises herbicide resistance and the resistance is conferred to an herbicide selected from the group consisting of imidazolinone, sulfonylurea, glyphosate, glufosinate, L-phosphinothricin, triazine, Clearfield, Dicamaba, 2,4-D, and benzonitrile.

10. The canola plant of claim 8, wherein the desired trait further comprises insect resistance and the insect resistance is conferred by a transgene encoding a *Bacillus thuringiensis* endotoxin.

11. The canola plant of claim 8, wherein the desired trait further comprises resistance to Blackleg, Fusarium wilt, or White Rust.

12. The canola plant of claim 8, wherein the plant comprises all of the physiological and morphological characteristics of canola cultivar DN040244, as shown in Tables 1, 2, and 3.

13. A method of modifying fatty acid metabolism or modifying carbohydrate metabolism of canola cultivar DN040244 wherein the method comprises: (a) crossing a DN040244 plant, wherein a representative sample of seed was deposited under ATCC Accession No. PTA-9289, with a plant of another canola cultivar to produce $F_1$ progeny plants that comprise a nucleic acid molecule encoding an enzyme selected from the group consisting of phytase, fructosyltransferase, levansucrase, alpha-amylase, invertase and starch branching enzyme or encoding an antisense of stearyl-ACP desaturase; (b) selecting one or more progeny plants that have said nucleic acid molecule to produce selected progeny plants; (c) crossing the selected progeny plants with the DN040244 plants to produce backcross progeny plants; (d) selecting for backcross progeny plants that have said nucleic acid molecule and physiological and morphological characteristics of canola cultivar DN040244 to produce selected backcross progeny plants; and (e) repeating steps (c) and (d) three or more times to produce selected fourth or higher backcross progeny plants that comprise said nucleic acid molecule and have an oleic acid value of about 70% and an α-linolenic acid value of less than about 3%.

14. The method of claim 13, wherein the plants further comprise a yield greater than about 2100 kg/ha, a protein value of greater than 45%, a glucosinolate value of less than 12%, or a chlorophyll value of less than 18%.

15. The method of claim 13, wherein the plants further comprise resistance to Blackleg (*Leptosphaeria maculans*), Fusarium wilt, or White Rust.

16. The method of claim 13, wherein the plants further comprise herbicide resistance to an herbicide selected from the group consisting of imidazolinone, sulfonylurea, glyphosate, glufosinate, L-phosphinothricin, triazine, Clearfield, Dicamaba, 2,4-D, and benzonitrile.

17. The method of claim 13, wherein the plants comprise all of the physiological and morphological characteristics of canola cultivar DN040244 as shown in Tables 1, 2 and 3.

18. A canola plant produced by the method of claim 13, wherein the plant comprises the nucleic acid molecule and has an oleic acid value of about 70% and an α-linolenic acid value of less than about 3%.

19. A canola plant produced by the method of claim 13, wherein the plants further comprise a yield greater than about 2100 kg/ha, a protein value of greater than 45%, a glucosinolate value of less than 12%, or a chlorophyll value of less than 18%.

20. A canola plant produced by the method of claim 13, wherein the plants comprise all of the physiological and morphological characteristics of canola cultivar DN040244 as shown in Tables 1, 2 and 3.

* * * * *